United States Patent [19]

Schumacher et al.

[11] Patent Number: 5,096,821

[45] Date of Patent: Mar. 17, 1992

[54] PYRUVATE OXIDASE MUTANTS, DNA EXPRESSING PYRUVATE OXIDASE AND METHODS OF USE THEREOF

[75] Inventors: Günther Schumacher, Bernried; Hans Moellering, Tutzing, both of Fed. Rep. of Germany

[73] Assignee: Boehringer Mannheim GmbH, Mannheim, Fed. Rep. of Germany

[21] Appl. No.: 670,362

[22] Filed: Mar. 14, 1991

Related U.S. Application Data

[63] Continuation of Ser. No. 416,593, Oct. 3, 1989, abandoned.

[30] Foreign Application Priority Data

Oct. 3, 1988 [DE] Fed. Rep. of Germany ....... 3833601

[51] Int. Cl.[5] .................................................. C12N 9/02
[52] U.S. Cl. ...................................... 435/191; 435/189
[58] Field of Search ................................ 435/189, 191

[56] References Cited

U.S. PATENT DOCUMENTS 4,666,832  5/1987  Elstner et al. ...................... 435/189

*Primary Examiner*—Douglas W. Robinson
*Assistant Examiner*—Marian C. Knode
*Attorney, Agent, or Firm*—Felfe & Lynch

[57] ABSTRACT

The present invention provides a pyruvate oxidase which decarboxylates pyruvate to form inter alia hydrogen peroxide and is active without the addition of FAD, thiamine pyrophosphate and divalent metal ions. The amino acid sequence of the enzyme changes at least one proline in position 178 and alanine in position 458 to a different amino acid. The present invention also provides a process for the preparation of this pyruvate oxidase and methods of use thereof.

5 Claims, 4 Drawing Sheets

FIG. 1A

```
  1  ATGGTTATGAAACAAACAAAACTAACATACTAGCAGTGCAGCAGTTATTAAAGTT   60
     MetValMetLysGlnThrLysGlnThrAsnIleLeuAlaGlyAlaAlaValIleLysVal

61  TTAGAAGCTTGGGGAGTAGATCATTTGTATGGTATTCCTGGAGGTTCAATTAATTCAATT  120
     LeuGluAlaTrpGlyValAspHisLeuTyrGlyIleProGlyGlySerIleAsnSerIle

121  ATGGACGCATTATCAGCAGAAAGGGATCGAATCCATTATATTCAAGTACGGCATGAAGAA  180
     MetAspAlaLeuSerAlaGluArgAspArgIleHisTyrIleGlnValArgHisGluGlu

181  GTTGGTGCAATGGCCGCCGCGCTGCTAAGCTAACGGGTAAAATCGGGGTTTGCTTC  240
     ValGlyAlaMetAlaAlaAlaAlaAspAlaLysLeuThrGlyLysIleGlyValCysPhe

241  GGCTCAGCGGGACCTGGTGGCACTCATCTTATGAATGGGTTATATGATGCGCGTGAAGAC  300
     GlySerAlaGlyProGlyThrHisLeuMetAsnGlyLeuTyrAspAlaArgGluAsp

301  CATGTCCCTGTTCTAGCACTTATTGGTCAATTTGGAACTACTGGGATGAACATGGATACG  360
     HisValProValLeuAlaLeuIleGlyGlnPheGlyThrThrGlyMetAsnMetAspThr

361  TTCCAAGAAATGAATGAGAATCCGATTTATGCGGACGTTGCAGATTATAATGTAACAGCC  420
     PheGlnGluMetAsnGluAsnProIleTyrAlaAspValAlaAspTyrAsnValThrAla

421  GTCAATGCTGCCACGTTGCCACATGTTATTGACGAAGCAATTCGACGCGCCTACGCGCAC  480
     ValAsnAlaAlaThrLeuProHisValIleAspGluAlaIleArgArgAlaTyrAlaHis

481  CAAGGTGTTGCGGTTGTGCAAATTCCAGTCGATTTACCATGGCAACAGATTCCAGCTGAA  540
     GlnGlyValAlaValValGlnIleProValAspLeuProTrpGlnIleProAlaGlu
```

FIG. 1B

| | | |
|---|---|---|
| 541 | GATTGGTATGCTTCCGCTAATAGTTATCCAGAACGCCGTTATTACCAGAACCCGACGTTCAA<br>AspTrpTyrAlaSerAlaAsnSerTyrGlnThrProLeuLeuProGluProAspValGln | 600 |
| 601 | GCAGTGACGAGATTGACACAGACTTTACTCGCAGCTGAACGCCACTTATTACTATGGC<br>AlaValThrArgLeuThrGlnThrLeuLeuAlaAlaGluArgProLeuIleTyrTyrGly | 660 |
| 661 | ATTGGAGCTCGTAAGGCTGGTAAAGAACTCGAACAATTGAGTAAAACGTGAAAATTCCA<br>IleGlyAlaArgLysAlaGlyLysGluLeuGluGlnLeuSerLysThrLeuLysIlePro | 720 |
| 721 | TTAATGAGTACGTATCCAGCTAAGGGTATTGTCGCGGATCGTTATCCAGCCTATTTGGGT<br>LeuMetSerThrTyrProAlaLysGlyIleValAlaAspArgTyrProAlaTyrLeuGly | 780 |
| 781 | TCTGCTAATCGGGTGGCACAAAAACCGGCGAATGAGGCACTTGCGCAAGCCGACGTTGTT<br>SerAlaAsnArgValAlaGlnLysProAlaAsnGluAlaLeuAlaGlnAlaAspValVal | 840 |
| 841 | TTATTTGTTGGTAATAATTATCCGTTTGCAGAAGTTTCCAAAGCGTTTAAAAATACGCGT<br>LeuPheValGlyAsnAsnTyrProPheAlaGluValSerLysAlaPheLysAsnThrArg | 900 |
| 901 | TATTTCTTACAAATTGATATTGATCCGGCTAAGTTAGGTAAACGACATAAAACAGATATT<br>TyrPheLeuGlnIleAspIleAspProAlaLysLeuGlyLysArgHisLysThrAspIle | 960 |
| 961 | GCGGTACTTGCTGATGCACAAAAGACGCTGCAATTTAGCACAGGTATCTGAACGG<br>AlaValLeuAlaAspAlaGlnLysThrLeuAlaIleLeuAlaGlnValSerGluArg | 1020 |
| 1021 | GAGTCGACACCTTGGTGGCAAGCCAATTTAGCCAATGTTAAAAATTGGCGGCTTATCTA<br>GluSerThrProTrpTrpGlnAlaAsnLeuAlaAsnValLysAsnTrpArgAlaTyrLeu | 1080 |

FIG. 1C

```
1081  GCTTCATTAGAAGATAAGCAGGAAGGGCCTTTACAAGCATATCAAGTGCTACGTGCCGTT   1140
      AlaSerLeuGluAspLysGlnGluGlyProLeuGlnAlaTyrGlnValLeuArgAlaVal

1141  AATAAAATTGCGGAGCCTGATGCAATTCTATTCGATTGTTGGTGATATCAATTTGAAT     1200
      AsnLysIleAlaGluProAspAlaIleLeuTyrSerIleAspValGlyAspIleAsnLeuAsn

1201  GCGAATCGACATTTGAAATTAACGCCACATTCCGCACATTACTTCTAACTTATTGCT      1260
      AlaAsnArgHisLeuLysLeuThrProSerAsnArgHisIleThrSerAsnLeuPheAla

1261  ACGATGGGAGTTGGTATTCCGGGAGCAATTGCTGCCAAACTTAATTATCCTGAGCGGCAG   1320
      ThrMetGlyValGlyIleProGlyAlaIleAlaAlaLysLeuAsnTyrProGluArgGln

1321  GTGTTTAATCTGGCCGGTGATGGTGGCCTTCGATGACCATGCAAGATTGGCGACGCAA    1380
      ValPheAsnLeuAlaGlyAspGlyGlyAlaSerMetThrMetGlnAspLeuAlaThrGln

1381  GTTCAATACCATTACCAGTGATTAATGTGTTTCACCAACTGCCAATATGGATTATC      1440
      ValGlnTyrHisLeuProValIleAsnValValPheThrAsnCysGlnTyrGlyPheIle

1441  AAAGATGAGCAGGAAGATACTAATCAGAATGATTTTATTGGCGTTGAATTCAATGATATT   1500
      LysAspGluGlnGluAspThrAsnGlnAsnAspPheIleGlyValGluPheAsnAspIle

1501  GATTTTAGTAAGATTGCCGATGCCGTGCACATGCAAGCTTTTCGAGTTAATAAGAAGATTGAG  1560
      AspPheSerLysIleAlaAspGlyValHisMetGlnAlaPheArgValAsnLysIleGlu

1561  CAATTACCCTGATGTTTTGAACAAGCCAAAGCAATCGCTCAGCATGAACCAGTTCTGATT   1620
      GlnLeuProAspValPheGluGlnAlaLysAlaIleAlaGlnHisGluProValLeuIle

1621  GATGCGGTGATTACAGGAGATCGGCCACTCGGCTGCTGAAAAGCTTCGTTTAGATTCGGCA   1680
      AspAlaValIleThrGlyAspArgProLeuProAlaGluLysLeuArgLeuAspSerAla

1681  ATGAGTTCGGCAGCTGATATTGAAGCATTAAACAACGGTATGAAGCTCAAGATTACAA    1740
      MetSerSerAlaAlaAspIleGluAlaLeuLysGlnArgTyrGluAlaGlnAspLeuGln

1741  CCACTTTCAACTTATTTAAAACAATTGGCTTAGATGATTGCAACATCAAATTGGACAG    1800
      ProLeuSerThrTyrLeuLysGlnPheGlyLeuAspAspLeuGlnHisGlnIleGlyGln

1801  GGTGGGTTTTAA  1812
      GlyGlyPheEnd
```

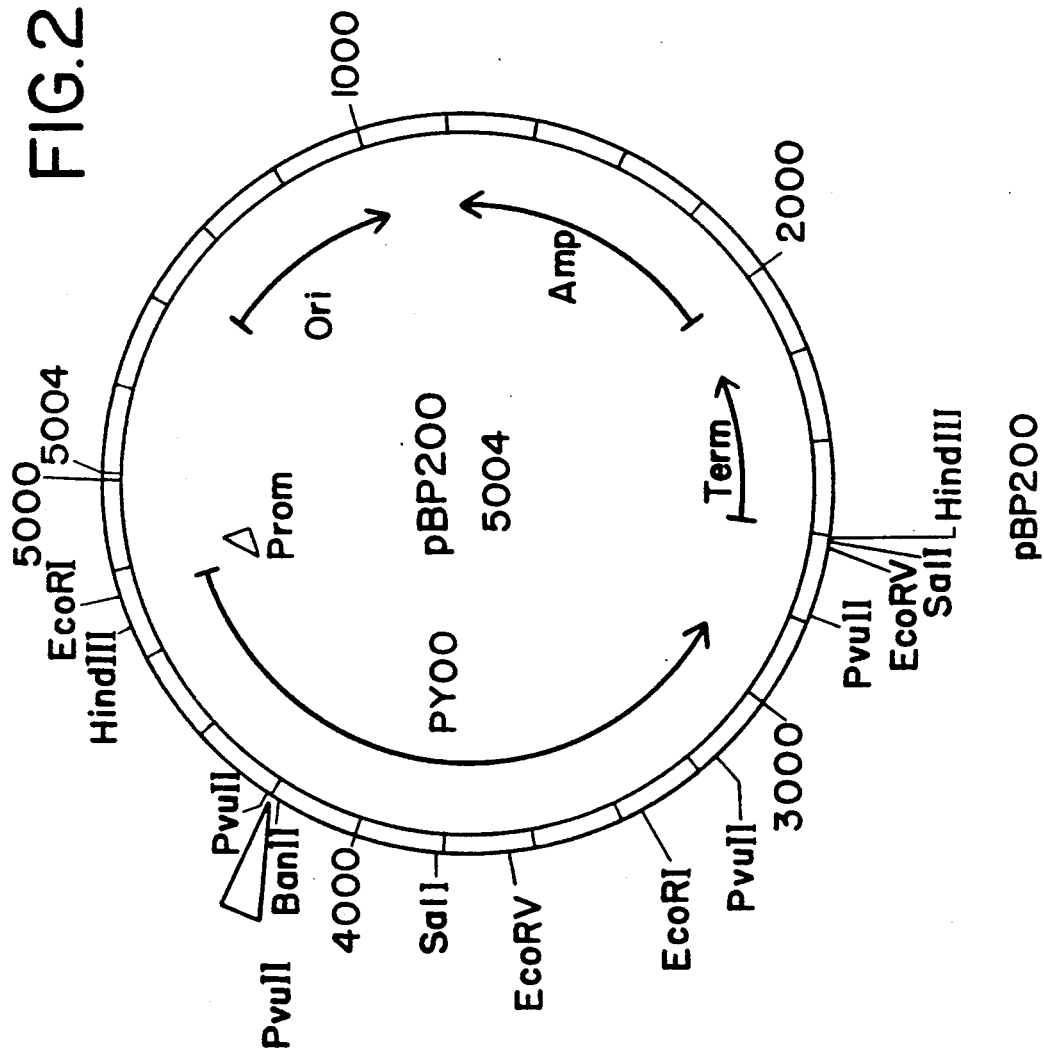

PYRUVATE OXIDASE MUTANTS, DNA EXPRESSING PYRUVATE OXIDASE AND METHODS OF USE THEREOF

This application is a continuation, of application Ser. No. 416,593, filed Oct. 3, 1989, now abandoned.

The present invention is concerned with pyruvate oxidase mutants, processes for the preparation thereof and reagents containing said mutants for the determination of pyruvate.

More particularly, the present invention is concerned with mutants of pyruvate oxidase which are more stable than the wild type enzyme and, therefore, are better suited for the enzymatic determination of pyruvate and of reactions which give rise to pyruvate.

Pyruvate oxidase (E.C. 1.2.3.3) is an enzyme which decarboxylates pyruvate in the presence of phosphate ions ("Pi") and oxygen with the formation of hydrogen peroxide *(Federation Proceedings,* 13, 734–738/1954). The reaction products, i.e., acetyl phosphate, carbon dioxide and especially hydrogen peroxide, can readily be detected analytically and, therefore, this enzyme is suitable for the quantitative determination of pyruvate and pyruvate-forming enzymes and of their substrates.

U.S. Pat. No. 4,666,832 teaches a pyruvate oxidase which is active without the addition of FAD, thiamine pyrophosphate (TPP) and divalent metal ions. In the presence of serum and magnesium ions, this enzyme does not form any insoluble precipitates and possesses excellent storage stability. However, it has been shown that in the presence of high salt concentrations in the serum, as well as at pH values of >7, this pyruvate oxidase only has limited stability.

Surprisingly, we have now found mutants of pyruvate oxidase from *Lactobacillus plantarum* (DSM 2571) which have better stability toward salts and in the alkaline pH range as compared to known forms of pyruvate oxidase.

Thus, according to the present invention, a mutant pyruvate oxidase is provided which decarboxylates pyruvate to form hydrogen peroxide and is active without the addition of FAD, thiamine pyrophosphate and divalent metal ions, characterized by at least one change selected from the group consisting of a change from proline in position 178 and alanine in position 458.

Especially preferred is a mutant enzyme having serine at position 178 and/or valine at position 458 of the amino acid sequence.

The mutant enzyme is characterized by a molecular weight of 250,000 (determined in an ultracentrifuge according to Ames), a pH optimum of 6.5 and $K_m$ with pyruvate (25° C.) of about 0.4 mmole/litre and a $K_m$ with phosphate (25° C.) of about 2.3 mmole/litre.

The mutant enzyme possesses residual activity of at least 45% in 0.1 mole/litre potassium phosphate buffer (pH 8) with 0.15 mole/litre sodium chloride after 30 minutes at 25° C.

Under these conditions, the preferred mutant enzyme shows residual activity of at least 70%. An especially preferred mutant enzyme displays residual activity of at least 85% under these conditions.

The preparation of the mutant enzymes according to the present invention takes place in that, according to known recombinant gene technology, a recombinant DNA which contains a pyruvate oxidase gene with essentially the sequence of the wild type enzyme (see FIG. 1 of the accompanying drawings) but additionally at least one change in the nucleotide base sequence at one of positions 532, 533, 534, 1372, 1373 and 1374 is incorporated into an expression vector. This change results in expression of a different amino acid in the position listed (i.e., 178 or 458). An appropriate host strain is transformed with this vector and is selected on the basis of expression of the expression vector. The thus transformed and selected strain is cultured under appropriate conditions and the mutant enzyme recovered from the culture medium.

The recombinant DNA preferably contains DNA where C (cystein) has been substituted by T (thymine) at at least one of bases 532 and base 1373, as compared to the nucleotide base sequence expressing known pyruvate oxidase.

The present invention also provides recombinant DNA which contains a pyruvate oxidase gene having a change in the nucleotide base sequence at one of positions 532, 533, 534, 1372, 1373 and 1374 as compared to the nucleotide base sequence expressing known pyruvate oxidase. Base 532 and/or base 1373 is preferably exchanged. Substitution of C for T at these positions is preferred.

However, any other substitution which results in the substitution of the amino acid at position 178 (proline) or the amino acid at position 458 (alanine) by any other amino acid is also covered herein. Substitution by serine (178) and valine (425) is especially preferred.

As recombinant DNA, especially preferred are plasmids pBP 201, pBP 202, pBP 203, pBP 203a and pBP 2006.

As host systems, both gram-positive and gram-negative micro-organisms can be used. Examples are *Bacillus spec.* or *Escherichia coli.* Micro-organisms of the species *Escherichia coli* are especially preferred. In particular, micro-organisms *Escherichia coli* Iaq I$^q$, (DSM 3689), (ED 8654), (DSM 2102), *Escherichia coli,* (DSM 4105), and *Escherichia coili,* (DMS 4106) are preferred. Vectors such as pBR 322 and derivatives are especially preferred as expression plasmids.

The present invention also provides the plasmids pBP 201, pBR 202, pBP 203, pBP 203 and pBP 2006. These contains the pyruvate oxidase gene of the wild, i.e., the known type (see FIG. 1) having changes in their DNA sequence as follows:

|  | base 532 from C to T | base 1274 from C to T | Change in 500 bp Ban II-EcoRV fragment |
| --- | --- | --- | --- |
| pBP 201 | + | − | − |
| pBP 202 | + | − | + |
| pBP 203 | + | + | − |
| pBP 203a | − | + | − |
| pBP 2006 | + | + | + |

The present invention also provides the DNA sequence of the wild type pyruvate oxidase which was not known until now. This DNA is contained in plasmid pBP 200 and is suitable as starting material for the preparation of the recombinant DNA according to the present invention.

The present invention is also concerned with the use of the mutant enzymes according to the present invention for the determination of pyruvate, pyruvate-forming enzymes and substrates thereof.

The determination of pyruvate preferably takes place by measuring hydrogen peroxide formed in the reaction scheme elaborated herein. Numerous suitable methods are known for this purpose which do not have to be described here in detail. It is also possible to measure the consumption of oxygen, for example by means of an oxygen electrode.

Typical examples of determinations which can be carried out with the enzyme according to the present invention are described in European Patent Specification No. 0,274,425 and include, for example, determination of glutamate-pyruvate transaminase, α-ketoglutarate, glutamate-oxalacetate transminase, pyruvate kinase, ADP, lactate dehydrogenase, lactic acid, glycerol, glycerol phosphate kinase, triglycerides, creatine phosphokinase, creatine, myokinase, thiokinase and fatty acids.

The present invention also provides a reagent for the determination of pyruvate which contains mutant enzymes according to the present invention, phosphate, a system for the determination of hydrogen peroxide, a buffer, and optionally a system for the formation of pyruvate.

As buffer there can be used any suitable buffer substance which buffers in the pH range of from about 5 to 9. Phosphate buffer is especially suitable. When a phosphate buffer is used, a separate source of inorganic phosophate is not required. In choosing the buffer, the pH values necessary for the adjuvant enzymes present in the system and other ingredients, such as chromophores must be considered. However, on the basis of the data known for these enzymes, an appropriate choice of buffer can readily be made by the skilled artisan.

The reagent according to the present invention is also suitable for the impregnation of carrier materials, for example papers, synthetic resins, films and the like, for making test strips.

The reagent according to the present invention preferably contains 1-50 U/ml mutant enzyme and 10-500 mmole/litre phosphate (pH 6-8).

The following examples are given for the purpose of illustrating the present invention.

EXAMPLE 1

Cells of *Escherichia coli* ED lac I⁹, DSM 3689 which contain one of the plasmids pBP 201, pBP 202, pBP 203, pBP 203a or pBP 2006 are cultured overnight at 28° to 30° C. in a 1 litre fermenter. As medium, there is used a complete medium (yeast/peptone extract) which contains 0.4% lactose and 100 mmole/litre phosphate (pH 7.5).

After centrifuging for 15 minutes at 8000 r.p.m., the cells are digested with lysozyme and the pyruvate oxidase is purified over DEAE-Sephadex and gel filtration (Sephacryl S 200).

EXAMPLE 2

Testing of the stability of the Enzyme in salt solution a) Activity determination

To test the stability of the enzyme, first the activity of the enzyme is determined on the basis of the following reactions:

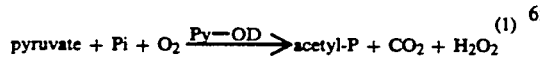

(1)

$H_2O_2$ + 4-aminoantipyrine (4AAP) + (2)

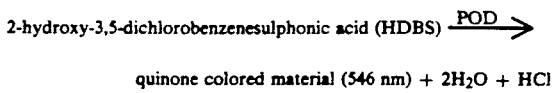

Hydrogen peroxide is consumed in equimolar amount relative to the colored material 1 U Py-OD = 1 μmole pyruvate reaction/min at 25° C.

The determination of the activity of the pyruvate oxidase (Py-OD) takes place with a reagent consisting of (end concentration in the test): 72 mmole/litre potassium phosphate buffer (pH 6.7); 8 mmole/litre 4-AAP; 6.8 mmole/litre HDBS; 50 mmole/litre pyruvate and 10 U/ml peroxidase (POD).

To 2 ml of this reagent is added 0.1 ml of the pyruvate oxidase solution to be tested and at 546 nm the extinction change per minute (ΔE/min) is determined at 25° C. with an optical path length of the solution of 1 cm. (ε = 16.5 cm²/umole). The activity is calculated according to the following equation:

$$\text{activity } (U) = \frac{\Delta E/\min \times V}{\epsilon}$$

$V$ = cuvette volume (cm³).

b) Stressing at pH 7.5

Pyruvate oxidase is stressed in an incubation solution consisting of 0.1 mole/litre potassium phosphate buffer (pH 7.5) and 0.15 mole/litre sodium chloride at 25° C. or 37° C. over the time given in the following Table I and the activity is determined in the manner described in Example 2(a). The results obtained are to be seen in Tables I/II. FIG. 2 of the accompanying drawings shows the results obtained after stressing at 37° C. for 20 hours at different pH values in 0.1 mole/liter potassium phosphate buffer. It follows therefrom that the pyruvate oxidases coded by the plasmids according to the present invention are superior to the wild type enzyme. The mutant pBP 2006, in particular, shows high stability towards alkaline pH values and to salts.

TABLE I

| | temperature 25° C. % residual activity after | |
| enzyme | 10 min | 30 min |
| --- | --- | --- |
| wild type | 28 | 5 |
| mutants | | |
| pBP 201 | 65 | 45 |
| pBP 202 | 89 | 70 |
| pBP 203 | 84 | 76 |
| pBP 2006 | 98 | 86 |

TABLE II

| | temperature 37° C. % residual activity after | | |
| enzyme | 5 min | 10 min | 20 min |
| --- | --- | --- | --- |
| wild type | 4 | 0 | 0 |
| mutants | | | |
| pBP 202 | 48 | 19 | 4 |
| pBP 203 | 45 | 18 | 5 |
| pBP 2006 | 65 | 36 | 34 |

EXAMPLE 3

Testing of the enzyme stability with undiluted serum 9.5 ml of undiluted serum are adjusted to the pH values given in the following Table III by the dropwise addition of 10% acetic acid or 2 mole/litre aqueous sodium hydroxide solution. Subsequently, 0.5 ml pyruvate oxidase solution (150 U/ml) is added thereto and a stressing at 37° C. carried out. The determination of the residual activity takes place as described in Example 2(a). The following Table III shows the results obtained.

TABLE III

| | residual activity after | | | | | |
|---|---|---|---|---|---|---|
| pH value | 1 min | 2 min | 5 min | 1 min | 2 min | 5 min |
| | wild type enzyme | | | pBP 2006 | | |
| 5.92 | 103 | 93.5 | 71.2 | 93.4 | 86.4 | 73.2 |
| 6.45 | 96.0 | 95.1 | 90.2 | 98.1 | 88.6 | 90.6 |
| 6.98 | 90.9 | 71.5 | 17.5 | 92.4 | 82.9 | 77.9 |
| 7.58 | 67.5 | 26.9 | 1.5 | 81.2 | 78.7 | 53.1 |
| 8.08 | 36.2 | 6.5 | — | 87.0 | 78.2 | 21.8 |
| 8.71 | 1.3 | — | — | 90.3 | 78.6 | 31.6 |

EXAMPLE 4

Testing of the stability of pyruvate oxidase from plasmid pBP 203a

Colonies of *Escherichia coli* laq I$^q$, DSM 3689, with and without plasmid pBP 203a, are cultured overnight on complete medium with cellulose filters. Subsequently, lysis is carried out with chloroform/toluene and the filters incubated for 20 minutes at 37° C. in 0.1 mole/litre potassium phosphate buffer (pH 7.5) and 0.15 mole/litre sodium chloride. The filters are then applied to plates which contain an indicator medium consisting of 40 mmole/litre sodium pyruvate, 0.24 mg/litre 4-aminoantipyrine, 1.5 mg/ml. N-ethyl-N-(3-methylphenyl)2-aminoethanesulphonic acid (EST), 1.25 µg/ml peroxidase, 1% agar and 50 mmole/litre potassium phosphate buffer (pH 7.2) and the color reaction observed after 1 minute. It is found that only colonies of micro-organisms which contain pBP 203a give a color reaction and consequently pyruvate oxidase is still present. The micro-organisms which contain the wild type plasmid no longer show a color reaction. This means that the pyruvate oxidase mutants from pBP 203a also show superior stability in comparison with the wild type enzyme.

EXAMPLE 5

Preparation of pyruvate oxidase mutant enzymes

Starting from the plasmid pBP 200 (production according to Example 6) which contains the wild type gene of pyruvate oxidase, the corresponding mutation is carried out on the DNA template with the method of directed mutagenesis. This process is described in detail in *Proc. Nat. Acad. Sci. USA*, 82, 488–492/1985 and *Nat. Enzymol.* 1987, as well as in Bulletin 1313 of Biorad Laboratories, Richmond, U.S.A. to Muta-Gene® in vitro mutagenesis kit.

For the preparation of pBP 201, oligonucleotide A with the following sequence was used:

5'-CGTTCAGCTGAAATCTGTTG-3'

For the preparation of pBP 203a, oligonucleotide B with the following sequence was used:

5'-AACTTGCGTCACCAAATCTT-3'

For the preparation of pBP 203, oligonucleotides A and B were used.

Plasmid pBP 202 which, like pBP 201, has a change of C to T at base 532, has, in addition a mutation on a 500 bp BenII/EcoRV fragment of the wild type gene. This plasmid has been deposited at the German Collection for Micro-organisms (DSM).

The plasmid pBP 2006 was prepared from pBP 202 by directed mutagenesis with the use of oligonucleotide B.

Further mutant enzymes are prepared by the use of oligonucleotide C:

5'-CGTTCAGCGCTAATCTGTTG-3'

(changing proline at 178 for serine) of oligonucleotide D:

5'-CGTTCAGCGACAATCTGTTG-3'

(changing proline at 178 for valine) of oligonucleotide E:

5'-CGTTCAGCAGCAATCTGTTG-3'

(changing proline at 178 for alanine) of oligonucleotide F:

5'-AACTTGCGTGGTCAAATCTT-3'

(changing alanine at 458 for threonine) of oligonucleotide G:

5'-AACTTGCGTAAGCAAATCTT-3'

(changing at alanine 458 for leucine of oligonucleotide H:

5'-AACTTGCGTGCCAAATCTT-3'

(changing of alanine 458 for glycine.

EXAMPLE 6

Preparation of pBP 200 (DSM 4875)

Plasmid pKK177-3 (DSM 3026) is cleaved with EcoRI and SmaI to form a first fragment. From the pyruvate oxidase-coding DNA fragment (FIG. 1) an approximately 1 kb EcoRI-SalI fragment and an approximately 1.2 kb SalI-Eco RV fragment are isolated. All three fragments are ligated with one another. This ligated product is transformed in *Escherichia coli* (DSM 3689) and selected for ampicillin resistance. The plasmid pBP 200 coding the pyruvate oxidase carries the restriction sites as given in FIG. 3 of the accompanying drawings.

Plasmid pBP 200 can also be obtained from plasmid pBP 202 by deletion of an approximately 2.2 kb-sized EcoRI-Eco RV fragment and replacement of this fragment by an approximately 1 kb-sized EcoRI-SalI and an approximately 1.2 kb-sized SalI-EcoRV fragment of the DNA according to FIG. 1 of the accompanying drawings.

It will be understood that the specification and examples are illustrative but not limitative of the present invention and that other embodiments within the spirit and scope of the invention will suggest themselves to those skilled in the art.

We claim:

1. Mutant pyruvate oxidase which catalyzes decarboxylation of pyruvate to form hydrogen peroxide in the absence of FAD, thiamin pyrophosphate and divalent metal ions, said mutant differing in its amino acid sequence as compared to pyruvate oxidase obtained from *Lactobacillus plantarium* DSM 2571 which catalyzes decarboxylation of pyruvate to form hydrogen peroxide in the absence of FAD, thiamin pyrophosphate and divalent metal ions at at least one of amino acid positions 178 and 458 of FIG. 1.

2. Mutant pyruvate oxidase of claim 1, having serine at amino acid position 178.

3. Mutant pyruvate oxidase of claim 1, having valine at amino acid position 458.

4. Mutant pyruvate oxidase of claim 1, having serine at amino acid position 178 and valine at amino acid position 458.

5. Mutant pyruvate oxidase of claim 1, characterized by a molecular weight of about 250,000, a pH optimum of about 6.5, a Km of about 0.4 mmol/liter with pyruvate at a temperature of about 25° C. and a Km of about 2.3 mmol/liter with phosphate at a temperature of about 25° C.

UNITED STATES PATENT AND TRADEMARK OFFICE
CERTIFICATE OF CORRECTION

PATENT NO. : 5,096,821

DATED : March 17, 1992

INVENTOR(S) : Gunther Schumacher et al.

It is certified that error appears in the above-identified patent and that said Letters Patent is hereby corrected as shown below:

Column 2, line 29: change "(425)" to -- 458 --;
          line 51: change "1274" to -- 1373 --.

Signed and Sealed this

Fourteenth Day of September, 1993

*Attest:*

BRUCE LEHMAN

*Attesting Officer*      *Commissioner of Patents and Trademarks*